US012359252B2

(12) United States Patent
Schutz et al.

(10) Patent No.: US 12,359,252 B2
(45) Date of Patent: Jul. 15, 2025

(54) COLORECTAL CANCER ASSOCIATED CIRCULATING NUCLEIC ACID BIOMARKERS (71) Applicant: CHRONIX BIOMEDICAL, San Jose, CA (US)

(72) Inventors: Ekkehard Schutz, Gottingen (DE); Julia Beck, Gottingen (DE); Howard Urnovitz, San Jose, CA (US)

(73) Assignee: Chronix Biomedical, San Jose, CA (US)

( * ) Notice: Subject to any disclaimer, the term of this patent is extended or adjusted under 35 U.S.C. 154(b) by 1541 days.

(21) Appl. No.: 16/007,795

(22) Filed: Jun. 13, 2018

(65) Prior Publication Data
US 2019/0136314 A1 May 9, 2019

Related U.S. Application Data (63) Continuation of application No. 15/798,362, filed on Oct. 30, 2017, now abandoned, which is a continuation of application No. 14/352,826, filed as application No. PCT/US2012/061044 on Oct. 19, 2012, now abandoned.

(60) Provisional application No. 61/550,098, filed on Oct. 21, 2011.

(51) Int. Cl.
C12Q 1/68 (2018.01)
C12Q 1/6874 (2018.01)
C12Q 1/6886 (2018.01)

(52) U.S. Cl.
CPC ......... *C12Q 1/6874* (2013.01); *C12Q 1/6886* (2013.01); *C12Q 2600/156* (2013.01)

(58) Field of Classification Search
CPC .................................................. C12Q 1/6886
See application file for complete search history.

(56) References Cited

U.S. PATENT DOCUMENTS

| | | | |
|---|---|---|---|
| 9,121,069 B2 | 9/2015 | Lo et al. | |
| 2003/0165895 A1 | 9/2003 | Czerniak et al. | |
| 2009/0162836 A1 | 6/2009 | Widschwendter | |
| 2009/0208942 A1 | 8/2009 | Liew et al. | |
| 2009/0215036 A1 | 8/2009 | Stropp et al. | |
| 2009/0280479 A1 | 11/2009 | Hoon et al. | |
| 2009/0297525 A1 | 12/2009 | Depinho et al. | |
| 2010/0136560 A1 | 6/2010 | Vogelstein et al. | |
| 2010/0184046 A1 | 7/2010 | Klass et al. | |
| 2014/0162888 A1* | 6/2014 | Kuslich ............ | G01N 33/57434 506/9 |

FOREIGN PATENT DOCUMENTS

| | | |
|---|---|---|
| WO | 2009/051842 A2 | 4/2009 |
| WO | 2010/053980 A2 | 5/2010 |
| WO | 2011/011426 A2 | 1/2011 |
| WO | 2011/130751 A1 | 10/2011 |

OTHER PUBLICATIONS

International Search Report and Written Opinion dated Jan. 18, 2013 for International Patent Application No. PCT/US2012/061044, 16 pages.
Extended European Search Report dated Jun. 1, 2015 for EP Application No. 12846333.8, 11 pages.
Boni et al., "Free circulating DNA as possible tumour marker in colorectal cancer", Surgical Oncology, vol. 19, pp. 29-31 (2007).
"GeneChip® Human Mapping 10K Array Xba 142 2.0", (Jan. 1, 2004) http://lib.cqvip.com/qk/81020X/201105/37770653.html (Retrieved on May 19, 2015).
Lecomte et al., "Detection of Free-Circulating Tumor-Associated DNA in Plasma of Colorectal Cancer Patients and Its Association with Prognosis", Int. J. Cancer, vol. 100, pp. 542-548 (2002).
Allen et al. "Role of cell-free plasma DNA as a diagnostic marker for prostate cancer", Ann. N.Y. Acad. Sci. 1022(1): 76-80 (2004).
Bastian et al., "Prognostic value of preoperative serum cell-0free circulating DNA in men with prostate cancer undergoing radical prostatectomy", Clinical Cancer Research 13(18):5361-5367 (2007).
Beck et al., "Next Generation Sequencing of Serum Circulating Nucleic Acids from Patients with Invasive Ductal Breast Cancer Reveals Differences to Healthy and Nonmalignant Controls," Mol Cancer Res, 8(3): 335-342 (2010).
Beck et al., "Profile of the Circulating DNA in Apparently Healthy Individuals," Clinical Chemistry, 55:4 (2009).
Ellinger et al.; "Noncancerous PTSG2 Dna fragments of apoptotic origin in sera of prostate cancer patients qualify as diagnostic and prognostic indicators"; Int. J. Cancer; 122:138-143 (Aug. 2007).
Felix et al., "Circulating tumour-associated plasma DNA represents an independent and informative predictor of prostate cancer", BJU Intl. 98(3): 544-548 (2006).
Muller et al.; "Comparison of genetic alterations detected in circulating microsatellite DNA in blood plasma samples of patients with prostate cancer and benign prostatic hyperplasia"; Ann. N.Y. Acad. Sci.; 1075:222-229 (2006).
Papadopoulou et al., "Cell-free DNA and RNA in plasma as a new molecular marker for prostate and breast cancer", Ann. N.Y. Acad. Sci. 1075: (2006).
Salani et al.; "Measurement of cyclin E genomic copy No. and strand length in cell-free DNA distinguish malignant versus benign effusions"; Clin. Cancer Res.; 13(19):5805-5809 (Oct. 2007).
Schutz et al., "Comparative analysis of the chromosomal origins of circulating nucleic acids in breast and prostate cancer," *J Clin Oncol* 28:15s (2010).
Schwarzenbach et al., "Cell-free tumor DNA in blood plasma as a marker for circulating tumor cells in prostate cancer", Clin. Cancer Res. 15(3): 1032-1038, (2009).

(Continued)

Primary Examiner — Kenneth R Horlick
(74) Attorney, Agent, or Firm — Kilpatrick Townsend & Stockton LLP (57) ABSTRACT The invention provides methods and reagents for diagnosing colorectal cancer that are based on the detection of biomarkers in the circulating nucleic acids from a patient to be evaluated.

5 Claims, 2 Drawing Sheets (56) References Cited

OTHER PUBLICATIONS

Sunami et al.; "Multimarker circulating DNA assay for assessing blood of prostate cancer patients"; *Clin. Chem.;* 55(3):559-567 (2009).
Umetani et al.; "Increased integrity of free circulating DNA in sera of patients with colorectal or periampullary cancer: direct quantitative PCR for ALU repeats"; *Clin. Chem.;* 52(6):1062-1069 (2006).

* cited by examiner

Figure 1-(con't)

C.

D.

COLORECTAL CANCER ASSOCIATED CIRCULATING NUCLEIC ACID BIOMARKERS

CROSS-REFERENCE TO RELATED APPLICATIONS

This application is a continuation of U.S. application Ser. No. 15/798,362, filed Oct. 30, 2017, now abandoned, which is a continuation of U.S. application Ser. No. 14/352,826, filed Apr. 18, 2014, now abandoned, which is a 371 stage of international application no. PCT/US2012/061044, filed Oct. 19, 2012, which claims priority benefit of U.S. provisional application No. 61/550,098, filed Oct. 21, 2011, each of which applications is herein incorporated by reference for all purposes.

BACKGROUND OF THE INVENTION

Colorectal cancer is the third most common cancer diagnosis in the United States and the second leading cause of cancer-related deaths. Methods to detect colorectal cancer, including colonoscopy and stool tests are available, however there are drawback to these various testing methods (see, e.g., McFarland et al., *Radiology* 248:717-720, 2008). There is a need for efficient detection methods. This invention addresses that need.

BRIEF SUMMARY OF THE INVENTION

The invention is based, in part, on the discovery of circulating nucleic acids (CNA) biomarkers associated with colorectal cancer. In some embodiments, the CNA biomarkers are polynucleotide fragments, e.g., DNA fragments, that are present at an elevated level in blood, e.g., in a serum or plasma sample, of a colorectal cancer patient in comparison to the level in blood, e.g., a serum or plasma sample, obtained from a normal individual who does not have colorectal cancer. In some embodiments, the CNA biomarkers are DNA polynucleotide sequences, i.e., DNA fragments that are present in blood, e.g., in a serum or plasma sample, at a decreased level of a colorectal cancer patient in comparison to the level in blood, e.g., serum or plasma, of a normal individual who does not have colorectal cancer.

Accordingly, in one aspect, the invention provides a method of analyzing CNA in a sample (blood, serum or plasma) from a patient comprising detecting the level of at least one cell-free DNA having a nucleotide sequence falling within a chromosomal region set forth in Table 2 in the sample. In some embodiments, detecting the level of the at least one biomarker comprises detecting a cell-free DNA molecule having between at least 20 to at least 500 consecutive nucleotides, or, e.g., between at least 50 and at least 400 consecutive nucleotides of a unique sequence within a chromosomal region as set forth in Table 2.

In one embodiment, a method of analyzing circulating free DNA in a patient sample is provided, comprising determining, in a sample that is blood, serum or plasma, the level of at least 2, 3, 4, 5, 7, 8, 9, 10, 15, 20, 30, 40, 45, 50, 55, 60, 65, 70, 75, 80 or 81 cell-free DNA molecules each having a sequence falling within a different chromosomal region set forth in Table 2, and preferably the sequences of the cell-free DNA molecules are free of repetitive element.

In another aspect, the present invention provides a kit including two or more (e.g., at least 2, 3, 4, 5, 7, 8, 9, 10, 15, 20, 30, 40, 45, 50, 55, 60, 65, 70, 75, 80, or 81) sets of oligonucleotides. In some embodiments, the kit includes 82 or fewer sets of oligonucleotides. Each set comprises one or more oligonucleotides with a nucleotide sequence falling within one single chromosomal region that is set forth in Table 2. Preferably, different oligonucleotide sets correspond to different chromosomal regions within Table 2. Preferably the oligonucleotides are free of repetitive elements. Optionally, the oligonucleotides are attached to one or more solid substrates such as microchips and beads.

In another aspect, the present invention provides a method of diagnosing or screening for colorectal cancer in a patient. The method includes the steps of: (a) detecting, in a sample that is blood, serum or plasma from a patient, the level of at least 2, 3, 4, 5, 7, 8, 9, 10, 15, 20, 30, 40, 45, 50, 55, 60, 65, 70, 75, 80 or 81 of the cell-free DNA molecules each having a sequence falling within a different chromosomal region set forth in Table 2; and (b) correlating the level of said first and second cell-free DNAs with an increased likelihood that the patient has colorectal cancer. Preferably, the sequences of the cell-free DNA molecules are free of repetitive elements.

In one aspect, the invention provides a method of identifying a patient that has a CNA biomarker associated with colorectal cancer, the method comprising detecting an increase in the level, relative to normal, of at least one biomarker designated as "UP" in Table 2 in a CNA sample obtained from serum or plasma from the patient. A biomarker can be identified using any number of methods, including sequencing of CNA as well as use of a probe or probe set to detect the presence of the biomarker.

In some embodiments, the invention provides a method of identifying a patient that has a CNA biomarker associated with colorectal cancer, the method comprising detecting a decrease in the level, relative to normal, of at least one biomarker designated as "DOWN" in Table 2 in a CNA sample from serum or plasma from the patient. A biomarker can be identified using any number of methods, including sequencing of CNA as well as use of a probe or probe set to detect the presence of the biomarker.

In a further aspect, the invention provides a kit for identifying a patient that has a biomarker for colorectal cancer, wherein the kit comprises at least one polynucleotide probe to a biomarker set forth in Table 2. Preferably, such a kit comprises probes to multiple biomarkers, e.g., at least 2, 3, 4, 5, 10, 20, 30, 40, 50, 55, 60, 65, 70, 75, 80, or all 81, of the biomarkers set forth in Table 2. In some embodiments, the kit also includes an electronic device or computer software to compare the hybridization patterns of the CNA in the patient sample to a colorectal cancer data set comprising a listing of the levels of biomarkers in colorectal cancer patients compared to normal individuals.

In some embodiments, the level of the at least one biomarker in CNA is determined by sequencing. In some embodiments, the level of the at least one biomarker in CNA is determined using an array. In some embodiments, the level of the at least one biomarker in CNA is determined using an assay that comprises an amplification reaction, such as a polymerase chain reaction (PCR). In some embodiments, a nucleic acid array forming a probe set comprising probes to two or more chromosomal regions set forth in Tables 2 is employed. In some embodiments, a nucleic acid array forming a probe set comprising 2, 3, 4, 5, 6, 7, 8, 9, 10, 15, 20, 25, 30, 35, 40, 45, 50, 55, 60, 65, 70, 75, 80, or all 81 of the chromosomal regions, set forth in Table 2 is employed.

In an additional aspect, the invention provides a method of detecting colorectal cancer in a patient that has, or is suspected of having, colorectal cancer, the method comprising contacting DNA from the serum or plasma sample with a probe that selectively hybridizes to a sequence, e.g., of at least 15, 20, 25, 50, 100, or 500, or greater, nucleotides in length present on a chromosomal region set forth in Table 2 under conditions in which the probe selectively hybridizes to the sequence; and detecting the level of hybridization of the probe, wherein the level of hybridization to the sequence is indicative of colorectal cancer.

DETAILED DESCRIPTION OF THE INVENTION

As used herein, a "biomarker" refers to a nucleic acid sequence that corresponds to a chromosomal region, where the level of the nucleic acid in CNA relative to normal is associated with colorectal cancer. In some embodiments, in which a biomarker is indicated as "UP" in Table 2, the level in CNA of a colorectal cancer patient is increased relative to normal. In some embodiments, in which a biomarker is indicated as "DOWN" in Table 2, the level in CNA of a colorectal cancer patient is decreased relative to normal.

In the current invention, a "chromosomal region" listed in Table 2 refers to the region of the chromosome that corresponds to the nucleotide positions indicated in the tables. The nucleotide positions on the chromosomes are numbered according to *Homo sapiens* (human) genome, hg18/build 36.1 genome version released March 2006. As understood in the art, there are naturally occurring polymorphisms in the genome of individuals. Thus, each chromosome region listed in Table 2 encompasses allelic variants as well as the particular sequence in the database. An allelic variant typically has at least 95% identity, often at least 96%, at least 97%, at least 98%, or at least 99% identity to the sequence of a chromosomal region that is present in a particular database, e.g., the National Center for Biotechnology Information (*Homo sapiens* Build 36.1 at the website http address www.ncbi.nlm.nih.gov/mapview/). Percent identity can be determined using well known algorithms, including the BLAST algorithm, e.g., set to the default parameters. Further, it is understood that the nucleotide sequences of the chromosomes may be improved upon as errors in the current database are discovered and corrected. The term "chromosomal region" encompasses any variant or corrected version of the same region as defined in Table 2. Given the information provided in Table 2 in the present disclosure and the available genome databases, a skilled person in the art will be able to understand the chromosomal regions used for the present invention even after new variants are discovered or errors are corrected.

"Detecting a chromosomal region" in CNA in the context of this invention refers to detecting the level of any sequence from a chromosomal region shown in Table 2, where the sequence detected can be assigned unambiguously to that chromosomal region. Thus, this term refers to the detection of unique sequences from the chromosomal regions. In the current invention, the level of at least one region, typically multiple regions used in combination, in a CNA sample is compared to the range found for such region in a group of "normal" individuals, i.e., in the context of this invention, individuals who do not have cancer or at least have not been diagnosed with cancer. For regions that are increased in level in colorectal cancer patients, i.e., regions listed as UP in Table 2, a result is typically considered to be increased if the result for the sample is higher than the $60^{th}$, $70^{th}$, $75^{th}$, $80^{th}$, $85^{th}$, $90^{th}$, $95^{th}$ or $99^{th}$ percentile. For regions that are decreased in level in colorectal cancer patients, i.e., regions listed as DOWN in Table 2, a result is typically considered to be decreased if the result for the sample is below the $40^{th}$, $30^{th}$, $25^{th}$, $20^{th}$, $15^{th}$, $10^{th}$, $5^{th}$, or $1^{st}$ percentile in normal individuals. Methods of removing repetitive sequences from the analysis are known in the art and include use of blocking DNA, e.g., when the target nucleic acids are identified by hybridization. In some embodiments, typically where the presence of a colorectal cancer biomarker is determined by sequencing the CNA from a patient, well known computer programs and manipulations can be used to remove repetitive sequences from the analysis (see, e.g., the EXAMPLES section). In addition, sequences that have multiple equally fitting alignment to the reference database are typically omitted from further analyses.

The term "detecting a biomarker" as used herein refers to detecting a polynucleotide, e.g., DNA, from a chromosomal region listed in Table 2 in CNA. As used herein, "detecting the level" of a biomarker encompasses quantitative measurements as well as detecting the presence, or absence, of the biomarker. Thus, e.g., the term "detecting an increase in the level of" a biomarker, relative to normal, includes qualitative embodiments in which the biomarker is detected in a patient sample, but not a normal sample. Similarly, the term "detecting a decrease in the level of" a biomarker, relative to normal, includes embodiments in which the biomarker is not detected in a patient sample, but is detected in normal samples. A biomarker is considered to be "present" if any nucleic acid sequence in the CNA is unambiguously assigned to the chromosomal region.

The term "unambiguously assigned" in the context of this invention refers to determining that a DNA detected in the CNA of a patient is from a particular chromosomal region. Thus, in detection methods that employ hybridization, the probe hybridizes specifically to that region. In detection methods that employ amplification, the primer(s) hybridizes specifically to that region. In detection methods that employ sequencing, the sequence is assigned to that region based on well-known algorithms for identity, such as the BLAST algorithm using high stringent parameters, such as e<0.0001. In addition, such a sequence does not have a further equally fitting hit on the used database.

The term "circulating nucleic acids" refers to acellular nucleic acids that are present in the blood.

The term "circulating cell-free DNA" as used herein means free DNA molecules of 25 nucleotides or longer that are not contained within any intact cells in human blood, and can be obtained from human serum or plasma.

The term "hybridization" refers to the formation of a duplex structure by two single stranded nucleic acids due to complementary base pairing. Hybridization can occur between exactly complementary nucleic acid strands or between nucleic acid strands that contain minor regions of mismatch. As used herein, the term "substantially complementary" refers to sequences that are complementary except for minor regions of mismatch. Typically, the total number of mismatched nucleotides over a hybridizing region is not more than 3 nucleotides for sequences about 15 nucleotides in length. Conditions under which only exactly complementary nucleic acid strands will hybridize are referred to as "stringent" or "sequence-specific" hybridization conditions.

Stable duplexes of substantially complementary nucleic acids can be achieved under less stringent hybridization conditions. Those skilled in the art of nucleic acid technology can determine duplex stability empirically considering a number of variables including, for example, the length and base pair concentration of the oligonucleotides, ionic strength, and incidence of mismatched base pairs. For example, computer software for calculating duplex stability is commercially available from National Biosciences, Inc. (Plymouth, Minn.); e.g., OLIGO version 5, or from DNA Software (Ann Arbor, Michigan), e.g., Visual OMP 6.

Stringent, sequence-specific hybridization conditions, under which an oligonucleotide will hybridize only to the target sequence, are well known in the art (see, e.g., the general references provided in the section on detecting polymorphisms in nucleic acid sequences). Stringent conditions are sequence-dependent and will be different in different circumstances. Generally, stringent conditions are selected to be about 5° C. lower to 5° C. higher than the thermal melting point (Tm) for the specific sequence at a defined ionic strength and pH. The Tm is the temperature (under defined ionic strength and pH) at which 50% of the duplex strands have dissociated. Relaxing the stringency of the hybridizing conditions will allow sequence mismatches to be tolerated; the degree of mismatch tolerated can be controlled by suitable adjustment of the hybridization conditions.

The term "primer" refers to an oligonucleotide that acts as a point of initiation of DNA synthesis under conditions in which synthesis of a primer extension product complementary to a nucleic acid strand is induced, i.e., in the presence of four different nucleoside triphosphates and an agent for polymerization (i.e., DNA polymerase or reverse transcriptase) in an appropriate buffer and at a suitable temperature. A primer is preferably a single-stranded oligodeoxyribonucleotide. The primer includes a "hybridizing region" exactly or substantially complementary to the target sequence, preferably about 15 to about 35 nucleotides in length. A primer oligonucleotide can either consist entirely of the hybridizing region or can contain additional features which allow for the detection, immobilization, or manipulation of the amplified product, but which do not alter the ability of the primer to serve as a starting reagent for DNA synthesis. For example, a nucleic acid sequence tail can be included at the 5' end of the primer that hybridizes to a capture oligonucleotide.

The term "probe" refers to an oligonucleotide that selectively hybridizes to a target nucleic acid under suitable conditions. A probe for detection of the biomarker sequences described herein can be any length, e.g., from 15-500 bp in length. Typically, in probe-based assays, hybridization probes that are less than 50 bp are preferred.

The term "target sequence" or "target region" refers to a region of a nucleic acid that is to be analyzed and comprises the sequence of interest.

As used herein, the terms "nucleic acid," "polynucleotide" and "oligonucleotide" refer to primers, probes, and oligomer fragments. The terms are not limited by length and are generic to linear polymers of polydeoxyribonucleotides (containing 2-deoxy-D-ribose), polyribonucleotides (containing D-ribose), and any other N-glycoside of a purine or pyrimidine base, or modified purine or pyrimidine bases. These terms include double- and single-stranded DNA, as well as double- and single-stranded RNA. Oligonucleotides for use in the invention may be used as primers and/or probes.

A nucleic acid, polynucleotide or oligonucleotide can comprise phosphodiester linkages or modified linkages including, but not limited to phosphotriester, phosphoramidate, siloxane, carbonate, carboxymethylester, acetamidate, carbamate, thioether, bridged phosphoramidate, bridged methylene phosphonate, phosphorothioate, methylphosphonate, phosphorodithioate, bridged phosphorothioate or sulfone linkages, and combinations of such linkages.

A nucleic acid, polynucleotide or oligonucleotide can comprise the five biologically occurring bases (adenine, guanine, thymine, cytosine and uracil) and/or bases other than the five biologically occurring bases. These bases may serve a number of purposes, e.g., to stabilize or destabilize hybridization; to promote or inhibit probe degradation; or as attachment points for detectable moieties or quencher moieties. For example, a polynucleotide of the invention can contain one or more modified, non-standard, or derivatized base moieties, including, but not limited to, N6-methyl-adenine, N6-tert-butyl-benzyl-adenine, imidazole, substituted imidazoles, 5-fluorouracil, 5 bromouracil, 5-chlorouracil, 5-iodouracil, hypoxanthine, xanthine, 4-acetylcytosine, 5 (carboxyhydroxymethyl)uracil, 5 carboxymethylaminomethyl-2-thiouridine, 5 carboxymethylaminomethyluracil, dihydrouracil, beta-D-galactosylqueosine, inosine, N6 isopentenyladenine, 1-methylguanine, 1-methylinosine, 2,2-dimethylguanine, 2-methyladenine, 2-methylguanine, 3-methylcytosine, 5-methyl cytosine, N6-methyladenine, 7-methylguanine, 5-methylaminomethyluracil, 5-methoxyaminomethyl-2-thiouracil, beta-D mannosylqueosine, 5'-methoxycarboxymethyluracil, 5-methoxyuracil, 2-methylthio-N6-isopentenyladenine, uracil-5-oxyacetic acid (v), wybutoxosine, pseudouracil, queosine, 2 thiocytosine, 5-methyl-2-thiouracil, 2-thiouracil, 4-thiouracil, 5-methyluracil, uracil-5-oxyacetic acidmethylester, 3-(3-amino-3-N-2-carboxypropyl) uracil, (acp3)w, 2,6-diaminopurine, and 5-propynyl pyrimidine. Other examples of modified, non-standard, or derivatized base moieties may be found in U.S. Pat. Nos. 6,001,611; 5,955,589; 5,844,106; 5,789,562; 5,750,343; 5,728,525; and 5,679,785, each of which is incorporated herein by reference in its entirety. Furthermore, a nucleic acid, polynucleotide or oligonucleotide can comprise one or more modified sugar moieties including, but not limited to, arabinose, 2-fluoro-arabinose, xylulose, and a hexose.

The term "repetitive element" as used herein refers to a stretch of DNA sequence of at least 25 nucleotides in length that is present in the human genome in at least 50 copies.

The terms "arrays," "microarrays," and "DNA chips" are used herein interchangeably to refer to an array of distinct polynucleotides affixed to a substrate, such as glass, plastic, paper, nylon or other type of membrane, filter, chip, bead, or any other suitable solid support. The polynucleotides can be synthesized directly on the substrate, or synthesized separate from the substrate and then affixed to the substrate. The arrays are prepared using known methods.

Introduction

The invention is based, at least in part, on the identification of nucleic acid biomarkers in CNA having sequences from particular chromosomal regions that are present in an increased level, relative to normal, in the blood of patients that have colorectal cancer. The invention is also based, in part, on the identification of biomarkers in the CNA that are present in a decreased level, relative to normal, in the blood of patients that have colorectal cancer. Thus, the invention provides methods and devices for analyzing the presence and level in CNA of polynucleotide molecules from a chromosomal region corresponding to at least one of the chromosomal regions set forth in Table 2.

Accordingly, in one aspect, the invention provides a method of analyzing CNA in a sample (blood, serum or plasma) from a patient comprising detecting a level of at least one circulating cell-free DNA having a nucleotide sequence of at least 25 nucleotides falling within a chromosomal region set forth in Table 2. Preferably, the circulating cell-free DNA is free of repetitive elements In one embodiment, the patient is an individual suspected of or diagnosed with cancer, e.g., colorectal cancer.

By "falling within" it is meant herein that the nucleotide sequence of a circulating cell-free DNA is substantially identical (e.g., greater than 95% identical) to a part of the nucleotide sequence of a chromosome region and can be unambiguously assigned to the chromosome region. In other words, the circulating cell-free DNA can hybridize to under stringent conditions, or be derived from, the chromosomal region.

In one embodiment, a method of analyzing circulating cell-free DNA in a patient sample is provided, comprising determining, in a sample that is blood, serum or plasma, a level of a plurality of circulating cell-free DNA molecules each having a sequence of at least 25 consecutive nucleotides in length, or at least 40, 50, 60, 75, or 100 or more consecutive nucleotides falling within the same one single chromosomal region set forth in Table 2. There may be two or more or any number of different circulating cell-free DNA molecules that are all derived from the same one chromosomal region set forth in Table 2, and in some embodiments, all such circulating cell-free DNA molecules are detected and the levels thereof are determined.

Preferably the sequences of the circulating cell-free DNA molecules are free of repetitive elements.

In one embodiment, a method of analyzing circulating cell-free DNA in a patient sample is provided, comprising determining, in a sample that is blood, serum or plasma, a level of at least 2, 3, 4, 5, 7, 8, 9, 10, 15, 20, 30, 40, 50, 55, 60, 65, 70, 75, or at least 80 or of 81 circulating cell-free DNA molecules each having a sequence of at least 25 consecutive nucleotides, or at least 40, 50 60, 75, or 100, or more consecutive nucleotides falling within a different chromosomal region set forth in Table 2. Preferably, the sequences of the circulating cell-free DNA molecules are free of repetitive elements. In preferred embodiments, the cell-free DNA molecules have sequences falling within different chromosomal regions in Table 2. In one specific embodiment, the levels of at least 2, 3, 4, 5, 7, 8, 9, 10, 15, 20, 25, 30, 35, 40, 45, 50, 55, 60, 65, 70, 75, or at least 80, or of 81, circulating cell-free DNA molecules are determined, the sequence of each falling within a different chromosomal region set forth in Table 2.

In a specific embodiment, the method of analyzing circulating cell-free DNA includes the steps of: isolating, from blood, serum or plasma sample of a patient, substantially all circulating cell-free DNA molecules having a length of at least 20, 25, 30, 40, 50, 75 or 100 consecutive nucleotides in length, or between 50 and 400 nucleotides in length, obtaining the sequence of each of the circulating cell-free DNA molecules, determining whether the sequence falls within a chromosomal region set forth in Table 2 and the level of said sequence.

In another specific embodiment, the method of analyzing circulating cell-free DNA includes the steps of: isolating, from blood, serum or plasma sample of a patient, substantially all circulating cell-free DNA molecules having a length of at least 20, 25, 30, 40, 50, 75 or 100 consecutive nucleotides in length, or between 50 and 400 nucleotides in length, and contacting the circulating cell-free DNA molecules to a plurality of oligonucleotides (e.g., on a DNA chip or microarray) to determine if one or more of the circulating cell-free DNA molecules hybridizes to any one of the plurality of oligonucleotide probes under stringent conditions. Each of the oligonucleotide probes has a nucleotide sequence identical to a part of the sequence of a chromosomal region set forth in Table 2. Thus, if a circulating DNA molecule hybridizes under stringent conditions to one of the oligonucleotide probes, it indicates that the circulating DNA molecule has a nucleotide sequence falling within a chromosomal region set forth in Table 2 and indicates the presence of the circulating DNA molecule. The level of the circulating DNA molecule can be determined by determining the amount of hybridized probe(s).

In the above various embodiments, preferably the circulating cell-free DNA molecules have at least 25 consecutive nucleotides in length (preferably at least 50, 70, 80, 100, 120 or 200 consecutive nucleotides in length). More preferably, the circulating cell-free DNA molecules have between about 50 and about 300 or 400, preferably from about 75 and about 300 or 400, more preferably from about 100 to about 200 consecutive nucleotides of a unique sequence within a chromosomal region as set forth in Table 2.

In another aspect, the present invention provides a method of diagnosing or screening for colorectal cancer in a patient. The method includes the steps of: (a) determining, in a sample that is blood, serum or plasma from a patient, the level of at least 1, 2, 3, 4, 5, 6, 7, 8, 9, 10, 15, 20, at least 30 or more, or of 35, circulating cell-free DNA molecules each having a sequence of at least 25 nucleotides in length falling within a different chromosomal region designated as "UP" Table 2; and (b) correlating the presence of an increased level of the circulating cell-free DNAs, relative to normal, with an increased likelihood that the patient has colorectal cancer.

In another embodiment, the method of invention includes the steps of: (a) determining, in a sample that is blood, serum or plasma from a patient, the level of at least 1, 2, 3, 4, 5, 6, 7, 8, 9, 10, 15, 20, 25, 30, 35, 40, of at least 45, or of 46, circulating cell-free DNA molecules each having a sequence of at least 25 nucleotides in length falling within a different chromosomal region designated as "DOWN" in Table 2; and (b) correlating the presence of a decreased level of the circulating cell-free DNAs, relative to normal, with an increased likelihood that the patient has colorectal cancer.

When the steps of the above methods are applied to a patient diagnosed with colorectal cancer, the patient may be monitored for the status of colorectal cancer, or for determining the treatment effect of a particular treatment regimen, or detecting cancer recurrence or relapse.

In the diagnosis/monitoring method of the present invention, preferably the sequences of the circulating cell-free DNA molecules are free of repetitive elements. In preferred embodiments, the cell-free DNA molecules have sequences falling within different chromosomal regions in set forth in Table 2.

In one embodiment, a method of diagnosing colorectal cancer in an individual is provided, comprising (a) determining the levels of at least 1, 2, 3, 4, 5, 6, 7, 8, 9, 10, 15, 20, at least 30 or more, or of 35, circulating cell-free DNA molecules each having a sequence of at least 25 nucleotides in length falling within a different chromosomal region designated as "UP" Table 2; and (b) correlating the presence of an increased level, relative to normal, of one or more of the circulating cell-free DNA molecules with an increased likelihood that the individual has colorectal cancer or a recurrence of colorectal cancer or a failure of treatment for colorectal cancer.

In one embodiment, a method of diagnosing/monitoring colorectal cancer in an individual is provided, comprising (a) determining the levels of at least 1, 2, 3, 4, 5, 6, 7, 8, 9, 10, 15, 20, 25, 30, 35, 40, of at least 45, or of 46, circulating cell-free DNA molecules each having a sequence of at least 25 nucleotides in length falling within a different chromosomal region designated as "DOWN" in Table 2; and (b) correlating the presence of a decreased level, relative to normal, of one or more of the circulating cell-free DNA molecules with an increased likelihood that the individual has colorectal cancer or a recurrence of colorectal cancer or a failure of treatment for colorectal cancer.

In yet another embodiment, the method of diagnosing, monitoring or screening for colorectal cancer in a patient, includes determining, in a sample that is blood, serum or plasma from the patient, the level of each and all circulating cell-free DNAs, each having a sequence falling within the same one single chromosomal region designated as "UP" in Table 2; and correlating an increased total level of said circulating cell-free DNAs, with an increased likelihood that said patient has colorectal, or recurrence of colorectal cancer. In other words, there can be any number of, and typically many, different circulating cell-free DNA molecules derived from one single same chromosomal region set forth in Table 2, and all of such different circulating cell-free DNA molecules are detected and the levels determined, and correlation with the status of colorectal cancer is made.

In another embodiment, the method of diagnosing, monitoring or screening for colorectal cancer in a patient, includes determining, in a sample that is blood, serum or plasma from the patient, the level of each and all circulating cell-free DNAs, each having a sequence falling within the same one single chromosomal region designated as "DOWN" in Table 2; and correlating a decreased level of said circulating cell-free DNAs with an increased likelihood that said patient has colorectal, or recurrence of colorectal cancer. In other words, there can be any number of, and typically many, different circulating cell-free DNA molecules derived from one single same chromosomal region set forth in Table 2, and all of such different circulating cell-free DNA molecules are detected and the level determined, and correlation with the status of colorectal cancer is made.

In a specific embodiment, substantially all circulating cell-free DNA molecules having a length of at least 20, 25, 30, 40, 50, 75 or 100 consecutive nucleotides in length, or between 50 and 400 nucleotides in length, are isolated from a blood, serum or plasma sample of a patient. The sequence of at least some representative portion of each of the isolated circulating cell-free DNA molecules is determined, and compared with one or more of the sequences of the chromosomal regions set forth in Table 2 to determine whether the sequence of a circulating cell-free DNA falls within a chromosomal region designated as "UP" in Table 2 and the level of the circulating DNA having said sequence. If the level is increased relative to normal, a diagnosis of colorectal cancer is made. In the case of a patient treated with a therapy for colorectal cancer, recurrence is indicated if an increase, relative to normal, in the level of a circulating cell-free DNA that falls within a chromosomal region designated as "UP" in Table 2 is detected. In preferred embodiments, a diagnosis of colorectal cancer or colorectal cancer treatment failure or recurrence is indicated if two or more circulating cell-free DNA molecules that fall within 2, 3, 4, 5, 6, 7, 8, 9, 10, or more chromosomal regions designated as "UP" in Table 2 are increased.

In another specific embodiment, substantially all circulating cell-free DNA molecules having a length of at least 20, 25, 30, 40, 50, 75 or 100 consecutive nucleotides in length, or between 50 and 400 nucleotides in length, are isolated from a blood, serum or plasma sample of a patient. These circulating cell-free DNA molecules, or a representative portion thereof, are hybridized to a microarray that is described above in the context of the kit invention to determine if one of the circulating cell-free DNA molecules hybridizes to any one of a plurality of oligonucleotide probes under stringent conditions. Each of the oligonucleotide probes has a nucleotide sequence identical to a part of the sequence of a chromosomal region designated as "UP" in Table 2. Thus, if a circulating DNA molecule hybridizes under stringent conditions to one of the oligonucleotide probes, it indicates that the circulating DNA molecule has a nucleotide sequence falling within a chromosomal region set forth in Table 2 and the level is determined. If the level is increased, relative to normal, a diagnosis of colorectal cancer is made. In the case of a patient treated with a therapy for colorectal cancer, recurrence is indicated if there is an increase in the level of a circulating cell-free DNA falls within a chromosomal region designated as "UP" in Table 2 is detected. In preferred embodiments, a diagnosis of colorectal cancer or colorectal cancer treatment failure or recurrence is indicated if two or more circulating cell-free DNA molecules fall within 2, 3, 4, 5, 6, 7, 8, 9, 10, or more chromosomal regions designated as "UP" in Table 2 are increased.

In a specific embodiment, substantially all circulating cell-free DNA molecules having a length of at least 20, 25, 30, 40, 50, 75 or 100 consecutive nucleotides in length, or between 50 and 400 nucleotides in length, are isolated from a blood, serum or plasma sample of a patient. The sequence of at least some representative portion of each of the isolated circulating cell-free DNA molecules is determined, and compared with one or more of the sequences of the chromosomal regions set forth in Table 2 to determine whether the sequence of a circulating cell-free DNA falls within a chromosomal region designated as "DOWN" in Table 2 and the level of the polynucleotide having said sequence. If the level is decreased relative to normal, a diagnosis of colorectal cancer is made. In the case of a patient treated with a therapy for colorectal cancer, recurrence is indicated if a decrease, relative to normal, in the level of a circulating cell-free DNA that falls within a chromosomal region designated as "DOWN" in Table 2 is detected. In preferred embodiments, a diagnosis of colorectal cancer or colorectal cancer treatment failure or recurrence is indicated if two or more circulating cell-free DNA molecules that fall within 2, 3, 4, 5, 6, 7, 8, 9, 10, or more chromosomal regions designated as "DOWN" in Table 2 are decreased.

In another specific embodiment, substantially all circulating cell-free DNA molecules having a length of at least 20, 25, 30, 40, 50, 75 or 100 consecutive nucleotides in length, or between 50 and 400 nucleotides in length, are isolated from a blood, serum or plasma sample of a patient. These circulating cell-free DNA molecules, or a representative portion thereof, are hybridized to a microarray that is described above in the context of the kit invention to determine if one of the circulating cell-free DNA molecules hybridizes to any one of a plurality of oligonucleotide probes under stringent conditions. Each of the oligonucleotide probes has a nucleotide sequence identical to a part of the sequence of a chromosomal region designated as "DOWN" in Table 2. Thus, if a circulating DNA molecule hybridizes under stringent conditions to one of the oligonucleotide probes, it indicates that the circulating DNA molecule has a nucleotide sequence falling within a chromosomal region set forth in Table 2 and the level is determined. If the level is decreased, relative to normal, a diagnosis of colorectal cancer is made. In the case of a patient treated with a therapy for colorectal cancer, recurrence is indicated if there is a decrease in the level of a circulating cell-free DNA falls within a chromosomal region designated as "DOWN" in Table 2 is detected. In preferred embodiments, a diagnosis of colorectal cancer or colorectal cancer treatment failure or recurrence is indicated if two or more circulating cell-free DNA molecules fall within 2, 3, 4, 5, 6, 7, 8, 9, 10, or more chromosomal regions designated as "UP" in Table 2 are decreased.

In the above various embodiments, preferably the circulating cell-free DNA molecules have at least 25 consecutive nucleotides in length (preferably at least 50, 70, 80, 100, 120 or 200 consecutive nucleotides in length). More preferably, the circulating cell-free DNA molecules have between about 50 and about 300 or 400, preferably from about 75 and about 300 or 400, more preferably from about 100 to about 200 consecutive nucleotides of a unique sequence within a chromosomal region as set forth in Table 2.

Detection of Circulating Nucleic Acids in the Blood

In order to detect the circulating nucleic acids in the blood of patients that may have, or are suspected of having, colorectal cancer, a blood sample is obtained from the patient. Serum or plasma from the blood sample is then analyzed for the presence and level of a circulating cell-free DNA or biomarker as described herein. Nucleic acids can be isolated from serum or plasma using well known techniques, see, e.g., the example sections. In the context of the current invention, the nucleic acid sequences that are analyzed are DNA sequences. Thus, in this section, methods described as evaluating "nucleic acids" refers to the evaluation of DNA.

Detection techniques for evaluating nucleic acids for the presence and level of a biomarker involve procedures well known in the field of molecular genetics. Further, many of the methods involve amplification of nucleic acids. Ample guidance for performing is provided in the art. Exemplary references include manuals such as PCR Technology: *Principles and Applications for DNA Amplification* (ed. H. A. Erlich, Freeman Press, NY, N.Y., 1992); *PCR Protocols: A Guide to Methods and Applications* (eds. Innis, et al., Academic Press, San Diego, Calif., 1990); Current Protocols in Molecular Biology, Ausubel, 1994-1999, including supplemental updates through April 2004; Sambrook & Russell, *Molecular Cloning, A Laboratory Manual* (3rd Ed, 2001).

Although the methods may employ PCR steps, other amplification protocols may also be used. Suitable amplification methods include ligase chain reaction (see, e.g., Wu & Wallace, *Genomics* 4:560-569, 1988); strand displacement assay (see, e.g., Walker et al., *Proc. Natl. Acad. Sci. USA* 89:392-396, 1992; U.S. Pat. No. 5,455,166); and several transcription-based amplification systems, including the methods described in U.S. Pat. Nos. 5,437,990; 5,409,818; and 5,399,491; the transcription amplification system (TAS) (Kwoh et al., *Proc. Natl. Acad. Sci. USA* 86:1173-1177, 1989); and self-sustained sequence replication (3SR) (Guatelli et al., *Proc. Natl. Acad. Sci. USA* 87:1874-1878, 1990; WO 92/08800). Alternatively, methods that amplify the probe to detectable levels can be used, such as Qβ-replicase amplification (Kramer & Lizardi, *Nature* 339:401-402, 1989; Lomeli et al., *Clin. Chem.* 35:1826-1831, 1989). A review of known amplification methods is provided, for example, by Abramson and Myers in *Current Opinion in Biotechnology* 4:41-47, 1993.

In some embodiments, the detection of biomarker in the CNA of a patient is performed using oligonucleotide primers and/or probes to detect a target sequence, wherein the target sequence is present in (e.g., comprises some unambiguously assigned portion of) any of the chromosomal regions listed in Table 2). Oligonucleotides can be prepared by any suitable method, usually chemical synthesis, and can also be purchased through commercial sources. Oligonucleotides can include modified phosphodiester linkages (e.g., phosphorothioate, methylphosphonates, phosphoamidate, or boranophosphate) or linkages other than a phosphorous acid derivative into an oligonucleotide may be used to prevent cleavage at a selected site. In addition, the use of 2'-amino modified sugars tends to favor displacement over digestion of the oligonucleotide when hybridized to a nucleic acid that is also the template for synthesis of a new nucleic acid strand.

In one embodiment, the biomarker is identified by hybridization under sequence-specific hybridization conditions with a probe that targets a chromosomal region, e.g., targets some unambiguously assigned portion of, any of the chromosomal regions listed in Table 2) described herein. The probe used for this analysis can be a long probe or sets for short oligonculeotide probes, e.g., from about 20 to about 150 nucleotides in length may be employed.

Suitable hybridization formats are well known in the art, including but not limited to, solution phase, solid phase, oligonucleotide array formats, mixed phase, or in situ hybridization assays. In solution (or liquid) phase hybridizations, both the target nucleic acid and the probe or primers are free to interact in the reaction mixture. Techniques such as real-time PCR systems have also been developed that permit analysis, e.g., quantification, of amplified products during a PCR reaction. In this type of reaction, hybridization with a specific oligonucleotide probe occurs during the amplification program to identify the presence of a target nucleic acid. Hybridization of oligonucleotide probes ensure the highest specificity due to thermodynamically controlled two state transition. Examples for this assay formats are fluorescence resonance energy transfer hybridization probes, molecular beacons, molecular scorpions, and exonuclease hybridization probes (e.g., reviewed in Bustin, *J. Mol. Endocrin.* 25:169-93, 2000).

Suitable assay formats include array-based formats, described in greater detail below in the "Device" section, where probe is typically immobilized. Alternatively, the target may be immobilized.

In a format where the target is immobilized, amplified target DNA is immobilized on a solid support and the target complex is incubated with the probe under suitable hybridization conditions, unhybridized probe is removed by washing under suitably stringent conditions, and the solid support is monitored for the presence of bound probe. In formats where the probes are immobilized on a solid support, the target DNA is typically labeled, usually during amplification. The immobilized probe is incubated with the amplified target DNA under suitable hybridization conditions, unhybridized target DNA is removed by washing under suitably stringent conditions, and the solid support/probe is monitored for the presence of bound target DNA.

In typical embodiments, multiple probes are immobilized on a solid support and the target chromosomal regions in the CNA from a patient are analyzed using the multiple probes simultaneously. Examples of nucleic acid arrays are described by WO 95/11995.

In an alternative probe-less method, amplified nucleic acid corresponding to a target nucleic acid present in a chromosomal region is performed using nucleic acid primers to the chromosomal region and is detected by monitoring the increase in the total level of double-stranded DNA in the reaction mixture, is described, e.g., in U.S. Pat. No. 5,994, 056; and European Patent Publication Nos. 487,218 and 512,334. The detection of double-stranded target DNA relies on the increased fluorescence various DNA-binding dyes, e.g., SYBR Green, exhibit when bound to double-stranded DNA.

As appreciated by one in the art, specific amplification methods can be performed in reaction that employ multiple primers to target the chromosomal regions such that the biomarker can be adequately covered.

DNA Sequencing

In preferred embodiments, a sequence from a chromosomal region set forth in Table 2 in the CNA from a patient undergoing evaluation is detected by direct sequencing. Such sequencing, especially using the Roche 454, Illumina, and Applied Biosystems sequencing systems mentioned below or similar advanced sequencing systems, can include quantitation of nucleic acids having a particular sequence to determine the level of a biomarker. In typical embodiments, CNA from a patient is sequenced using a large-scale sequencing method that provides the ability to obtain sequence information from many reads. Such sequencing platforms includes those commercialized by Roche 454 Life Sciences (GS systems), Illumina (e.g., HiSeq, MiSeq) and Applied Biosystems (e.g., SOLiD systems).

The Roche 454 Life Sciences sequencing platform involves using emulsion PCR and immobilizing DNA fragments onto bead. Incorporation of nucleotides during synthesis is detected by measuring light that is generated when a nucleotide is incorporated.

The Illumina technology involves the attachment of randomly fragmented genomic DNA to a planar, optically transparent surface. Attached DNA fragments are extended and bridge amplified to create an ultra-high density sequencing flow cell with clusters containing copies of the same template. These templates are sequenced using a sequencing-by-synthesis technology that employs reversible terminators with removable fluorescent dyes.

Methods that employ sequencing by hybridization may also be used. Such methods, e.g., as used in the Applied Biosystems SOLiD4+ technology, involves emulsion PCR that immobilizes DNA fragments onto beads followed by the use of a pool of all possible oligonucleotides of a fixed length, labeled according to the sequenced position. Oligonucleotides are annealed and ligated; the preferential ligation by DNA ligase for matching sequences results in a signal informative of the nucleotide at that position.

The sequence can be determined using any other DNA sequencing method including, e.g., methods that use semiconductor technology to detect nucleotides that are incorporated into an extended primer by measuring changes in current that occur when a nucleotide is incorporated (see, e.g., U.S. Patent Application Publication Nos. 20090127589 and 20100035252). Other techniques include direct label-free exonuclease sequencing in which nucleotides cleaved from the nucleic acid are detected by passing through a nanopore (Oxford Nanopore) (Clark et al., *Nature Nanotechnology* 4: 265-270, 2009); and Single Molecule Real Time (SMRT™) DNA sequencing technology (Pacific Biosciences), which is a sequencing-by synthesis technique.

Devices and Kits

In a further aspect, the invention provides diagnostic devices and kits useful for identifying and determining the level of one or more colorectal cancer-associated biomarkers in the CNA from a patient where the one or more biomarkers has a sequence unambiguously assigned to any of the chromosomal regions set forth in Table 2. As will be apparent to skilled artisans, the kit of the present invention is useful in the above-discussed method for analyzing circulating cell-free DNA in a patient sample and in diagnosing, screening or monitoring colorectal cancer as described above.

Thus, in one aspect, the present invention provides the use of at least one oligonucleotide for the manufacture of a diagnostic kit useful in diagnosing, screening or monitoring colorectal cancer. The nucleotide sequence of the oligonucleotide falls within a chromosomal region set forth in Table 2.

Preferably, the kit of the present invention includes one, two or more (e.g., at least 1, 2, 3, 4, 5, 6, 7, 8, 9, 10, 12, 15, 20, 25, 30, 40 or at least 50, but preferably less than 81, preferably from one to about 50, more preferably from 2 to about 50, or from 3 to about 50 sets of oligonucleotides. Each set comprises one or more oligonucleotides (e.g., from about one to about 10,000, preferably from 50, 100, 200 or 300 to about 10,000). All of the nucleotide sequences of such one or more oligonucleotides in each set fall within the same one single chromosomal region that is set forth in Table 2 (or match a part of the same one single sequence set forth in Table A). Each oligonucleotide should have from about 18 to 100 nucleotides, or from 20 to about 50 nucleotides, and is capable of hybridizing, under stringent hybridization conditions, to the chromosomal region in which its sequence falls. The oligonucleotides are useful as probes for detecting circulating cell-free DNA molecules derived from the chromosomal regions. Preferably, each set includes a sufficient number of oligonucleotides with sequences mapped to one chromosomal region such that any circulating cell-free DNA molecules derived from the chromosomal region can be detected with the oligonucleotide set. Thus, the number of oligonucleotides required in each set is determined by the total length of unique nucleotide sequence of a particular chromosomal region, as will be apparent to skilled artisans. Such total lengths are indicated in Table 2.

Preferably, in the kit of the present invention, different oligonucleotide sets correspond to different chromosomal regions within the same table. Preferably, the oligonucleotides are free of repetitive element. Optionally, the oligonucleotides are attached to one or more solid substrates such as microchips and beads. In preferred embodiments, the kit is a microarray with the above oligonucleotides.

Use of the oligonucleotides included in the kit described for the manufacture of the kit useful for diagnosing, screening or monitoring colorectal cancer is also contemplated. The manufacturing of such kit should be apparent to a skilled artisan.

In some embodiments, a diagnostic device comprises probes to detect at least 2, 3, 4, 5, 6, 7, 8, 9, 10, 15, 20, 30, 40, 50, 60, 75, 80, or all 81 chromosomal regions set forth in Table 2. In some embodiments, the present invention provides probes attached to a solid support, such as an array slide or chip, e.g., as described in DNA Microarrays: A Molecular Cloning Manual, 2003, Eds. Bowtell and Sambrook, Cold Spring Harbor Laboratory Press. Construction of such devices are well known in the art, for example as described in US Patents and Patent Publications U.S. Pat. No. 5,837,832; PCT application W095/11995; U.S. Pat. Nos. 5,807,522; 7,157,229, 7,083,975, 6,444,175, 6,375,903, 6,315,958, 6,295,153, and 5,143,854, 2007/0037274, 2007/0140906, 2004/0126757, 2004/0110212, 2004/0110211, 2003/0143550, 2003/0003032, and 2002/0041420. Nucleic acid arrays are also reviewed in the following references: Biotechnol Annu Rev 8:85-101 (2002); Sosnowski et al, Psychiatr Genet 12(4):181-92 (December 2002); Heller, Annu Rev Biomed Eng 4: 129-53 (2002); Kolchinsky et al, Hum. Mutat 19(4):343-60 (April 2002); and McGail et al, Adv Biochem Eng Biotechnol 77:21-42 (2002).

Any number of probes may be implemented in an array. A probe set that hybridizes to different, preferably unique, segments of a chromosomal region may be used where the probe set detects any part of the chromosomal region. Alternatively, a single probe to a chromosomal region may be immobilized to a solid surface. Polynucleotide probe can be synthesized at designated areas (or synthesized separately and then affixed to designated areas) on a substrate, e.g., using a light-directed chemical process. Typical synthetic polynucleotides can be about 15-200 nucleotides in length.

The kit can include multiple biomarker detection reagents, or one or more biomarker detection reagents in combination with one or more other types of elements or components (e.g., other types of biochemical reagents, containers, packages such as packaging intended for commercial sale, substrates to which biomarker detection reagents are attached, electronic hardware components, etc.). Accordingly, the present invention further provides biomarker detection kits and systems, including but not limited to arrays/microarrays of nucleic acid molecules, and beads that contain one or more probes or other detection reagents for detecting one or more biomarkers of the present invention. The kits can optionally include various electronic hardware components; for example, arrays ("DNA chips") and microfluidic systems ("lab-on-a-chip" systems) provided by various manufacturers typically comprise hardware components. Other kits may not include electronic hardware components, but may be comprised of, for example, one or more biomarker detection reagents (along with, optionally, other biochemical reagents) packaged in one or more containers.

Biomarker detection kits/systems may contain, for example, one or more probes, or sets of probes, that hybridize to a nucleic acid molecule present in a chromosomal region set forth in Table 2.

A biomarker detection kit of the present invention may include components that are used to prepare CNA from a blood sample from a patient for the subsequent amplification and/or detection of a biomarker.

Correlating the Presence of Biomarkers with Colorectal Cancer

The present invention provides methods and reagents for detecting the level of a biomarker in CNA from a patient that has colorectal cancer or that is being evaluated to determine if the patient may have colorectal cancer. In the context of the invention, "detection" or "identification" or "identifying the presence" or "detecting the presence" of a biomarker associated with colorectal cancer in a CNA sample from a patient refers to determining any level of the biomarker in the CNA of the patient where the level is greater than a threshold value that distinguishes between colorectal cancer and non-colorectal cancer CNA samples for a given assay.

In the current invention, for example, an increase in the level of any one of the chromosomal regions (i.e., biomarkers) designated as "UP" in Table 2 is indicative of colorectal cancer. In some embodiments, a biomarker may have been observed to be present infrequently in CNA obtained from normal individuals; however, given the low frequency of occurrence in normal samples relative to a higher frequency of occurrence in colorectal cancer, the presence of the biomarker in a patient indicates that the patient has a greater likelihood, e.g., 95% or greater likelihood, of having colorectal cancer.

The biomarkers designated as "UP" in Table 2 are associated with colorectal cancer, i.e., they are over-represented in colorectal cancer patients compared to individuals not diagnosed with colorectal cancer. Thus, the detection of an increase, relative to non-colorectal cancer patients, in the level of one or more of the biomarkers designated as "UP" in Table 2 is indicative of colorectal cancer, i.e., the patient has an increased probability of having colorectal cancer compared to a patient that does not have an increase in the level of the biomarker. In some embodiments, the detection and increase in the level of two or more biomarkers designated as "UP" in Table 2 in the CNA of a patient is indicative of a greater probability for colorectal cancer. As understood in the art, other criteria, e.g., clinical criteria, etc., are also employed to diagnose colorectal cancer in the patient. Accordingly, patients that have a biomarker associated with colorectal cancer also undergo other diagnostic procedures. In some embodiments, the patient is administered a therapeutic agent for colorectal cancer, such as one or more chemotherapeutic agents, e.g., 5-fluorouracil, leucovorin, or oxaliplatin or capecitabine; and/or a monoclonal antibody, such as bevacizumab, cetuximab, or panitumumab, or alternative monoclonal antibody.

The biomarkers designated as "DOWN" in Table 2 are associated with colorectal cancer, i.e., they are under-represented in colorectal cancer patients compared to individuals not diagnosed with colorectal cancer. Thus, the detection of a decrease, relative to non-colorectal cancer patients, in the level of one or more of the biomarkers designated as "DOWN" in Table 2 is indicative of colorectal cancer, i.e., the patient has an increased probability of having colorectal cancer compared to a patient that does not have a decrease in the level of the biomarker. In some embodiments, a biomarker may have been observed to be present infrequently in CNA obtained from cancer patients; however, given the low frequency of occurrence in cancer samples relative to a higher frequency of occurrence in normal individuals, the presence of the biomarker in a patient indicates that the patient has a decreased likelihood, e.g., 5% or less likelihood, of having colorectal cancer. As understood in the art, other criteria, e.g., clinical criteria, etc., are also employed to diagnose colorectal cancer in the patient. Accordingly, patients that have a biomarker associated with colorectal cancer also undergo other diagnostic procedures. In some embodiments, the patient is administered a therapeutic agent for colorectal cancer, such as one or more chemotherapeutic agents, e.g., 5-fluorouracil, leucovorin, or oxaliplatin or capecitabine; and/or a monoclonal antibody, such as bevacizumab, cetuximab, or panitumumab, or alternative monoclonal antibody.

"Over-represented" or "increased level" means that the level of one or more circulating cell-free DNAs is higher than normal levels. Generally this means an increase in the level as compared to an index value. Conversely "under-represented" or "decreased level" means that the level of one or more particular circulating cell-free DNA molecules is lower than normal levels. Generally this means a decrease in the level as compared to an index value.

In preferred embodiments, the test value representing the level of a particular circulating cell-free DNA is compared to one or more reference values (or index values), and optionally correlated to colorectal cancer or cancer recurrence. Optionally, an increased likelihood of colorectal cancer is indicated if the test value is greater than the reference value for CNA listed as "UP" in Table 2 or less than the reference value for CNA listed as "DOWN" in Table 2.

Those skilled in the art are familiar with various ways of deriving and using index values. For example, the index value may represent the copy number or concentration of a particular cell-free DNA listed as "UP" in Table 2 in a blood sample from a patient of interest in a healthy state, in which case a copy number or concentration in a sample from the patient at a different time or state significantly higher (e.g., 1.01-fold, 1.05-fold, 1.10-fold, 1.2-fold, 1.3-fold, 1.4-fold, 1.5-fold, 1.6-fold, 1.7-fold, 1.8-fold, 1.9-fold, 2-fold, 3-fold, 4-fold, 5-fold, 10-fold, 20-fold, 30-fold, 40-fold, 50-fold, 100-fold or more higher) than this index value would indicate, e.g., colorectal cancer or increased likelihood of colorectal cancer recurrence. In some embodiments, the level of the CNA is "increased" if it is at least 1, 2, 3, 4, 5, 10, 15, 20 or more standard deviations greater than the index value in normal subjects. In some embodiments, an index value may represent the copy number or concentration of a particular cell-free DNA listed as "DOWN" in Table 2 in a blood sample from a patient of interest in a healthy state, in which case a copy number or concentration in a sample from the patient at a different time or state significantly lower (e.g., 1.01-fold, 1.05-fold, 1.10-fold, 1.2-fold, 1.3-fold, 1.4-fold, 1.5-fold, 1.6-fold, 1.7-fold, 1.8-fold, 1.9-fold, 2-fold, 3-fold, 4-fold, 5-fold, 10-fold, 20-fold, 30-fold, 40-fold, 50-fold, 100-fold or more lower) than this index value would indicate, e.g., colorectal cancer or increased likelihood of colorectal cancer recurrence. In some embodiments the level of the CNA is "decreased" if it is at least 1, 2, 3, 4, 5, 10, 15, 20 or more standard deviations lower than the index value in normal subjects.

Alternatively, the index value may represent the average concentration or copy number of a particular circulating cell-free DNA for a set of individuals from a diverse cancer population or a subset of the population. For example, one may determine the average copy number or concentration of a circulating cell-free DNA in a random sampling of patients with colorectal cancer. Thus, patients having a copy number or concentration (test value) comparable to or higher than, this value identified as having an increased likelihood of having colorectal cancer or colorectal cancer recurrence than those having a test value lower than this value.

A useful index value may represent the copy number or concentration of a particular circulating cell-free DNA or of a combination (weighted or straight addition) of two or more circulating cell-free DNAs corresponding to the same chromosomal region or different chromosomal regions. When two or more biomarkers or circulating cell-free DNA molecules are used in the diagnosis/monitoring method, the level of each biomarker or circulating cell-free DNA can be weighted and combined. Thus, a test value may be provided by (a) weighting the determined level of each circulating cell-free DNA molecule with a predefined coefficient, and (b) combining the weighted level to provide a test value. The combining step can be either by straight addition or averaging (i.e., weighted equally) or by a different predefined coefficient.

The information obtained from the biomarker analysis may be stored in a computer readable form. Such a computer system typically comprises major subsystems such as a central processor, a system memory (typically RAM), an input/output (I/O) controller, an external device such as a display screen via a display adapter, serial ports, a keyboard, a fixed disk drive via a storage interface and a floppy disk drive operative to receive a floppy disc, and a CD-ROM (or DVD-ROM) device operative to receive a CD-ROM. Many other devices can be connected, such as a network interface connected via a serial port.

The computer system may also be linked to a network, comprising a plurality of computing devices linked via a data link, such as an Ethernet cable (coax or 10 BaseT), telephone line, ISDN line, wireless network, optical fiber, or other suitable signal transmission medium, whereby at least one network device (e.g., computer, disk array, etc.) comprises a pattern of magnetic domains (e.g., magnetic disk) and/or charge domains (e.g., an array of DRAM cells) composing a bit pattern encoding data acquired from an assay of the invention.

The computer system can comprise code for interpreting the results of a study evaluating the presence of one or more of the biomarkers. Thus in an exemplary embodiment, the biomarker analysis results are provided to a computer where a central processor executes a computer program for determining the likelihood of a patient that has colorectal cancer.

The invention also provides the use of a computer system, such as that described above, which comprises: (1) a computer; (2) a stored bit pattern encoding the biomarker testing results obtained by the methods of the invention, which may be stored in the computer; (3) and, optionally, (4) a program for determining the likelihood of a patient having colorectal cancer.

The invention further provides methods of generating a report based on the detection of one or more biomarkers set forth in Table 2.

Thus, the present invention provides systems related to the above methods of the invention. In one embodiment the invention provides a system for analyzing circulating cell-free DNA, comprising: (1) a sample analyzer for executing the method of analyzing circulating cell-free DNA in a patient's blood, serum or plasma as described in the various embodiments above (incorporated herein by reference); (2) a computer system for automatically receiving and analyzing data obtained in step (1) to provide a test value representing the status (concentration or copy number) of one or more circulating cell-free DNA molecules having a nucleotide sequence of at least 25 nucleotides falling within a chromosomal region set forth in Table 2, and optionally for comparing the test value to one or more reference values each associated with a predetermined status of colorectal cancer. In some embodiments, the system further comprises a display module displaying the comparison between the test value and the one or more reference values, or displaying a result of the comparing step.

Thus, as will be apparent to skilled artisans, the sample analyzer may be, e.g., a sequencing machine (e.g., Illumina HiSeq™, Ion Torrent PGM, Applied Biosystems SOLiD™ sequencer, PacBio RS, Helicos Heliscope™, etc.), a PCR machine (e.g., Applied Biosystems 7900, Fluidigm BioMark™, etc.), a microarray instrument, etc.

In one embodiment, the sample analyzer is a sequencing instrument, e.g., a next-generation sequencing instrument such as Roche's GS systems, Illumina's HiSeq and MiSeq, and Applied Biosystems' SOLiD systems. Circulating cell-free DNA molecules are isolated from a patient's blood or serum or plasma, and the sequences of all of the circulating cell-free DNA molecules are obtained using the sample analyzer. The sequencing instrument is used in sequencing the circulating cell-free DNA molecules, and obtaining the sequences of these molecules. A computer system is then employed for automatically analyzing the sequences to determine the level of a circulating cell-free DNA molecule having a nucleotide sequence of at least 25 nucleotides falling within a chromosomal region set forth in Table 2 in the sample. For example, the computer system may compare the sequence of each circulating cell-free DNA molecule in the sample to the sequence, available in the human sequence database, of the chromosomal region to determine if there is a match, i.e., if the sequence of a circulating cell-free DNA molecule falls within a chromosomal region set forth in Table 2. The copy number of a particular circulating cell-free DNA molecule is also automatically determined by the computer system. Optionally the computer system automatically correlates the sequence analysis result with a diagnosis regarding colorectal cancer. For example, if one, and preferably two or more, circulating cell-free DNA molecules are identified to be derived from chromosomal regions designated as "UP" in Table 2 and present at an increased level, then the computer system automatically correlates this analysis result with a diagnosis of colorectal cancer. If one, and preferably two or more, circulating cell-free DNA molecules are identified to be derived from chromosomal regions designated as "DOWN" in Table 2 and present at a decreased level, then the computer system automatically correlates this analysis result with a diagnosis of colorectal cancer. Optionally, the computer system further comprises a display module displaying the results of sequence analysis and/or the result of the correlating step. The display module may be for example, a display screen, such as a computer monitor, TV monitor, or the touch screen, a printer, and audio speakers.

The computer-based analysis function can be implemented in any suitable language and/or browsers. For example, it may be implemented with C language and preferably using object-oriented high-level programming languages such as Visual Basic, SmallTalk, C++, and the like. The application can be written to suit environments such as the Microsoft Windows™ environment including Windows™ 98, Windows™ 2000, Windows™ NT, and the like. In addition, the application can also be written for the MacIntosh™, SUN™, UNIX or LINUX environment. In addition, the functional steps can also be implemented using a universal or platform-independent programming language. Examples of such multi-platform programming languages include, but are not limited to, hypertext markup language (HTML), JAVA™, JavaScript™, Flash programming language, common gateway interface/structured query language (CGI/SQL), practical extraction report language (PERL), AppleScript™ and other system script languages, programming language/structured query language (PL/SQL), and the like. Java™- or JavaScript™-enabled browsers such as HotJava™, Microsoft™ Explorer™, or Netscape™ can be used. When active content web pages are used, they may include Java™ applets or ActiveX™ controls or other active content technologies.

The analysis function can also be embodied in computer program products and used in the systems described above or other computer- or internet-based systems. Accordingly, another aspect of the present invention relates to a computer program product comprising a computer-usable medium having computer-readable program codes or instructions embodied thereon for enabling a processor to carry out the analysis and correlating functions as described above. These computer program instructions may be loaded onto a computer or other programmable apparatus to produce a machine, such that the instructions which execute on the computer or other programmable apparatus create means for implementing the functions or steps described above. These computer program instructions may also be stored in a computer-readable memory or medium that can direct a computer or other programmable apparatus to function in a particular manner, such that the instructions stored in the computer-readable memory or medium produce an article of manufacture including instruction means which implement the analysis. The computer program instructions may also be loaded onto a computer or other programmable apparatus to cause a series of operational steps to be performed on the computer or other programmable apparatus to produce a computer implemented process such that the instructions which execute on the computer or other programmable apparatus provide steps for implementing the functions or steps described above.

The following examples are provided by way of illustration only and not by way of limitation. Those of skill in the art will readily recognize a variety of non-critical parameters that could be changed or modified to yield essentially similar results.

EXAMPLES

Example 1. Identification of Colorectal Cancer-Associate CNA

Study Samples

The study evaluated 68 serum samples obtained from patients with colorectal cancer and 72 serum samples from healthy controls. Patient serum samples were obtained from two different sites: Cleveland Clinic satellite facility in Florida, USA (n=16) and Ryazan Central Oblast Hospital, Russia (n=47). Blood was drawn preoperatively from treatment-naïve patients under local IRB approval and processed as described previously (Beck et al., *Clin. Chem.* 55:730-738, 2009). Normal samples were obtained from the department of Transfusion Medicine of the Georg-August University of Göttingen (n=12), the Ryazan Central Oblast Hospital (n=50), Asterand plc., Detroit, MI, USA, (n=8), and an additional two volunteers.

Construction of Sequencing Libraries

After extraction of DNA from serum or plasma, using a standard silica-based method, a whole genome amplification was performed in duplicate. The products of the two reactions were pooled and used for further analysis. The P2 adapter used for sequencing and a 10 bp sample-specific nucleotide sequence (also referred to as molecular barcode) are added by PCR using fusion-primers. Two consecutive PCRs with different fusion-primers were performed; the total number of cycles was four. Following the PCRs, the tagged DNA of 43 samples (Pool 1) or 49 samples (Pool 2 and 3) was pooled and all further preparations were performed on this pooled DNA material. Further library preparation steps were as follows:

i) Restriction of DNA with endonuclease NlaIII;
ii) Removal of the 3' overhangs created by NlaIII using the Large Klenow Fragment;
iii) Ligation of P1 (second sequencing adapter) to the blunted ends;
iv) Amplification of the library using primers complementary to the P1/P2 adapters of the fragments; and
v) Size-selection using the iBase electrophoresis system and 2% E-Gel size selection agarose gels (Invitrogen) to obtain fragments in the range of 150-250 bp.

Sequencing

Sequencing of the libraries was performed on a SOLiD4+ Instrument (Applied Biosystems) equipped with an EZBead-System (Applied Biosystems) for conducting the emulsion PCRs. All necessary reagents were purchased from Applied Biosystems. Emulsion PCRs and sequencing was performed as recommended by the manufacturer. For each fragment, 50 bp and 10 bp of molecular barcode were sequenced.

Data Analysis

The sequence reads were assigned to the different samples according to the sequence of the molecular barcode.

The sequences were mapped to the human genome (Build 36.1/Hg18) using the BioScope software suite (Applied Biosystems) using the default parameterization for 50 bp reads. Briefly, the local mapping algorithm of the software employing a 25 bases seeding scheme with two serial seedings starting from base 1 and base 16 was used. During extension of the seeds, a match received a score of 1 and a mismatch received a score of −2. For reads that mapped to more than one position within the genome, the best mapping position was recorded when its quality score was five-fold better than the quality score of the second best mapping (clear zone procedure). All mapping results were recorded for each individual sample. The number of reads mapped in genomic windows of 100,000 bp was determined. The windows (each of 100,000 bp in size) were moved along the chromosomes by intervals of 50,000 bp starting at a position of 200,000 of each chromosome in order to exclude telomere regions. One tabulated text file was produced for each of the human chromosomes and each sample. The tabulated text file contained the following information:
  i) Chromosome-ID
  ii) WindowStart
  iii) WindowStop
  iv) Number of mapped reads Each line contained information for one window. These data were used for an unsupervised cluster search in 300 independent rounds of random selection of training sets, consisting of 60% of each of the disease and control groups.

Selection of Genomic Clusters

The first step of the unsupervised cluster search (UCS) was:
  1) Normalization of the reads (per sample)
    a. Global→total reads as basis
    b. Local→read per chromosome as basis For 300 rounds, the data were randomized into training (60%) and validation set (40%). The training sets were used to:
  1) Optimize clusters that segregated disease from control group by
    a. Combining consecutive clusters (add reads)
    b. Stopping at maximum of either:
      i. #disease<smallest control
      ii. #disease>largest control
  2) Record when optimum were found and #disease>12, otherwise go to 3):
    a. Normalization (Global/Local)
    b. Chromosome
    c. Optimized region (start-stop)
    d. #disease samples positive in training set
    e. #disease samples positive in validation set using:
      i. delimiter from training set
      ii. delimiter from validation set (according to 1(b.)
    f. values for each sample in (segregated disease/control)
      i. training set
      ii. validation set
  3) Perform analysis on next window The next randomization was performed and the data recorded into a new table.

For each of the 300 runs, performance in the validation set was tested by calling each normalized read for any significant region in that set positive if greater then the controls or less than the controls respectively. A positively called region was set to "1", a not-positive was set to "0" for each sample and region.

Definition of Final Clusters Segregating Controls from Colorectal Cancer:

All regions identified from the UCS above were ranked according to their number of occurrences in the 300 rounds. Overlapping or regions were combined and duplications were removed.

In three runs of SOLiD4+ sequencing, 1,170,174,163 reads were generated. For the control group an average $6.3 \times 10^6$ (SD: $2.2 \times 10^6$) reads per sample were mappable to the human genome database version HG18. In the colorectal cancer group, the average was $5.2 \times 10^6$ (SD: $1.6 \times 10^6$).

The 300 rounds of random training/validation sets, show a separation of the groups in the validation set as given in the table. The AUCs of ROC curves for each round was constructed by using the sum of read calls under different conditions (e.g., global and local normalization and up or down in disease).

The data in Table 1 show AUCs from ROC curves with standard deviations.

TABLE 1

| | Global | | | Local | | |
|---|---|---|---|---|---|---|
| | All | Up | Down | All | Up | Down |
| AUC Mean | 88.5% | 88.9% | 87.6% | 88.1% | 86.7% | 90.1% |
| StDev | 5.9% | 5.8% | 7.4% | 5.8% | 6.0% | 5.2% |

Figure 1:
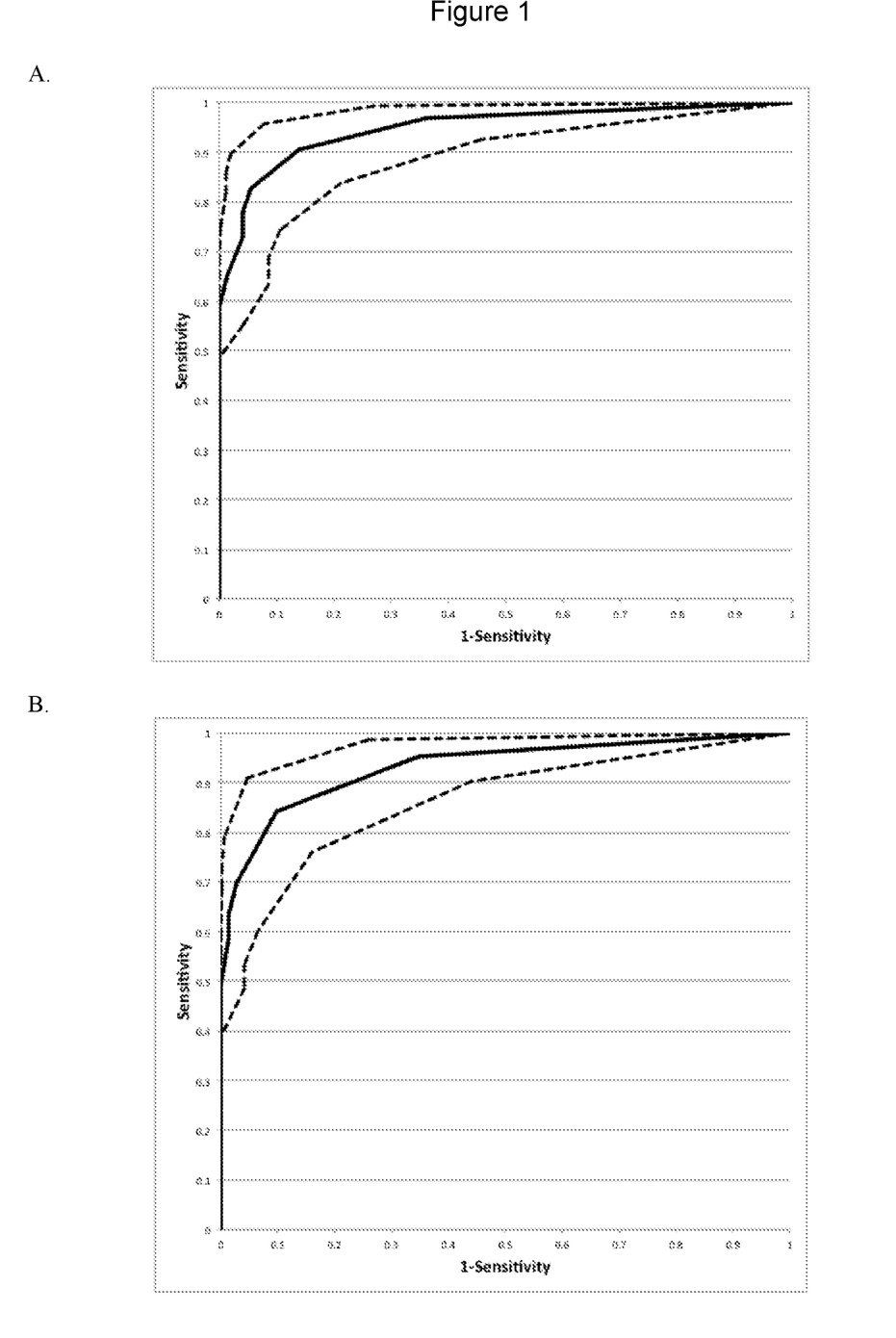
FIG. 1 provides an example of ROC curves for the various combinations of regions. Panel A: Global Normalization all regions (46) AUC: 0.95 0.88-0.99; Panel B: Local Normalization all regions (35) AUC: 0.93 0.86-0.98; Panel C: Direction Up (35) AUC: 0.93 0.87-0.97; Panel D: Direction Down (46) AUC: 0.92 0.84-0.97.

A final model was constructed from the 300 rounds and applied to all samples. The biomarker regions for colorectal cancers defined in this way are provided in Table 2. These regions can be used in different combination for detection of sample status. The "Rank" is calculated from the number of randomizations (see, above) in which a region was identified. The graphs presented in FIG. 1 with the AUC values are based on the combination of such regions, called positive at 95% specificity level.

TABLE 2

| Direction | Norm | HS | Region | Rank |
|---|---|---|---|---|
| UP | GLOBAL | 1 | 69800001-70200000 | 31 |
| UP | GLOBAL | 1 | 196550001-196800000 | 74 |
| UP | GLOBAL | 2 | 34550001-34950000 | 74 |
| UP | GLOBAL | 3 | 154600001-155050000 | 38 |
| UP | GLOBAL | 3 | 34350001-34550000 | 48 |
| UP | GLOBAL | 3 | 133900001-134350000 | 55 |
| UP | GLOBAL | 4 | 27550001-27800000 | 7 |
| UP | GLOBAL | 5 | 18650001-18950000 | 47 |
| UP | GLOBAL | 5 | 85650001-85950000 | 50 |
| UP | GLOBAL | 5 | 90850001-91100000 | 66 |
| UP | GLOBAL | 6 | 114250001-114550000 | 25 |
| UP | GLOBAL | 7 | 87000001-87300000 | 14 |
| UP | GLOBAL | 7 | 11350001-11700000 | 16 |
| UP | GLOBAL | 7 | 19600001-20100000 | 38 |

TABLE 2-continued

| Direction | Norm | HS | Region | Rank |
|---|---|---|---|---|
| UP | GLOBAL | 7 | 95100001-95400000 | 71 |
| UP | GLOBAL | 8 | 51450001-52000000 | 22 |
| UP | GLOBAL | 8 | 61100001-61450000 | 34 |
| UP | GLOBAL | 8 | 82850001-83200000 | 78 |
| UP | GLOBAL | 9 | 75350001-75600000 | 50 |
| UP | GLOBAL | 12 | 44700001-45050000 | 31 |
| UP | GLOBAL | 14 | 21350001-22050000 | 20 |
| DOWN | GLOBAL | 1 | 180850001-181150000 | 23 |
| DOWN | GLOBAL | 2 | 234900001-235400000 | 8 |
| DOWN | GLOBAL | 2 | 26950001-27450000 | 12 |
| DOWN | GLOBAL | 2 | 95200001-95550000 | 53 |
| DOWN | GLOBAL | 2 | 105100001-105400000 | 55 |
| DOWN | GLOBAL | 3 | 53950001-54200000 | 11 |
| DOWN | GLOBAL | 3 | 140050001-140200000 | 74 |
| DOWN | GLOBAL | 4 | 183950001-184250000 | 18 |
| DOWN | GLOBAL | 5 | 2400001-2800000 | 29 |
| DOWN | GLOBAL | 5 | 134800001-135050000 | 59 |
| DOWN | GLOBAL | 7 | 65150001-65350000 | 66 |
| DOWN | GLOBAL | 8 | 30200001-30600000 | 34 |
| DOWN | GLOBAL | 8 | 10200001-11250000 | 2 |
| DOWN | GLOBAL | 9 | 100200001-100550000 | 61 |
| DOWN | GLOBAL | 10 | 500001-800000 | 31 |
| DOWN | GLOBAL | 10 | 114450001-114750000 | 36 |
| DOWN | GLOBAL | 10 | 123650001-124100000 | 19 |
| DOWN | GLOBAL | 12 | 127350001-127950000 | 5 |
| DOWN | GLOBAL | 15 | 72150001-72400000 | 64 |
| DOWN | GLOBAL | 16 | 68250001-68800000 | 10 |
| DOWN | GLOBAL | 16 | 19350001-19800000 | 30 |
| DOWN | GLOBAL | 16 | 49650001-49950000 | 37 |
| DOWN | GLOBAL | 16 | 13050001-13500000 | 45 |
| DOWN | GLOBAL | 20 | 47500001-47900000 | 54 |
| DOWN | GLOBAL | 22 | 31000001-31200000 | 42 |
| UP | LOCAL | 1 | 86600001-87150000 | 12 |
| UP | LOCAL | 1 | 69650001-70250000 | 9 |
| UP | LOCAL | 2 | 34550001-35100000 | 71 |
| UP | LOCAL | 3 | 154600001-154950000 | 42 |
| UP | LOCAL | 3 | 107600001-107850000 | 74 |
| UP | LOCAL | 5 | 85650001-85950000 | 41 |
| UP | LOCAL | 6 | 142250001-142450000 | 50 |
| UP | LOCAL | 6 | 106850001-107000000 | 55 |
| UP | LOCAL | 7 | 87000001-87350000 | 26 |
| UP | LOCAL | 9 | 75350001-75600000 | 48 |
| UP | LOCAL | 10 | 68500001-69050000 | 61 |
| UP | LOCAL | 17 | 42750001-43100000 | 78 |
| UP | LOCAL | 19 | 19850001-20300000 | 66 |
| UP | LOCAL | 20 | 8000001-8250000 | 78 |
| DOWN | LOCAL | 1 | 180850001-181100000 | 61 |
| DOWN | LOCAL | 2 | 234900001-235400000 | 6 |
| DOWN | LOCAL | 2 | 105100001-105400000 | 45 |
| DOWN | LOCAL | 3 | 53950001-54200000 | 16 |
| DOWN | LOCAL | 4 | 183900001-184300000 | 4 |
| DOWN | LOCAL | 5 | 173400001-173700000 | 58 |
| DOWN | LOCAL | 6 | 163600001-163850000 | 66 |
| DOWN | LOCAL | 7 | 129100001-129550000 | 42 |
| DOWN | LOCAL | 7 | 65150001-65350000 | 59 |
| DOWN | LOCAL | 7 | 98000001-98650000 | 64 |
| DOWN | LOCAL | 7 | 153600001-153950000 | 78 |
| DOWN | LOCAL | 8 | 10200001-11400000 | 1 |
| DOWN | LOCAL | 8 | 30200001-30700000 | 23 |
| DOWN | LOCAL | 8 | 124600001-124950000 | 40 |
| DOWN | LOCAL | 9 | 100150001-100650000 | 15 |
| DOWN | LOCAL | 10 | 500001-800000 | 28 |
| DOWN | LOCAL | 10 | 123650001-124200000 | 20 |
| DOWN | LOCAL | 10 | 114450001-114750000 | 66 |
| DOWN | LOCAL | 12 | 127350001-128100000 | 3 |
| DOWN | LOCAL | 15 | 72150001-72400000 | 71 |
| DOWN | LOCAL | 16 | 78050001-78250000 | 26 |

All patents, patent applications, and other published reference materials cited in this specification are hereby incorporated herein by reference in their entirety for their disclosures of the subject matter in whose connection they are cited herein.

What is claimed is:
1. A method of treating colorectal cancer in a patient, comprising:
(a) sequencing cell-free DNA in a sample obtained from the patient, wherein the sample is blood, serum or plasma;
(b) quantifying the level of at least a first cell-free DNA and a second cell-free DNA, wherein each of the first and the second cell-free DNA has a sequence at least 25 nucleotides in length free of repetitive elements, wherein the first cell-free DNA is unambiguously assigned to a first chromosomal region selected from the group consisting of chromosomal regions 1-81 set forth as follows, and the second cell-free DNA is unambiguously assigned to a second chromosomal region selected from the group consisting of chromosomal regions 1-81 that is different from the first chromosomal region, said regions numbered according to National Center for Biotechnology Information *Homo sapiens* hg18/Build 36.1:

| | chromosome | region |
|---|---|---|
| 1 | 1 | 69800001-70200000 |
| 2 | 11 | 196550001-196800000 |
| 3 | 2 | 34550001-34950000 |
| 4 | 3 | 154600001-155050000 |
| 5 | 3 | 34350001-34550000 |
| 6 | 3 | 133900001-134350000 |
| 7 | 4 | 27550001-27800000 |
| 8 | 5 | 18650001-18950000 |
| 9 | 5 | 85650001-85950000 |
| 10 | 5 | 90850001-91100000 |
| 11 | 6 | 114250001-114550000 |
| 12 | 7 | 87000001-87300000 |
| 13 | 7 | 11350001-11700000 |
| 14 | 7 | 19600001-20100000 |
| 15 | 7 | 95100001-95400000 |
| 16 | 8 | 51450001-52000000 |
| 17 | 8 | 61100001-61450000 |
| 18 | 8 | 82850001-83200000 |
| 19 | 9 | 75350001-75600000 |
| 20 | 12 | 44700001-45050000 |
| 21 | 14 | 21350001-22050000 |
| 22 | 1 | 180850001-181150000 |
| 23 | 2 | 234900001-235400000 |
| 24 | 2 | 26950001-27450000 |
| 25 | 2 | 95200001-95550000 |
| 26 | 2 | 105100001-105400000 |
| 27 | 3 | 53950001-54200000 |
| 28 | 3 | 140050001-140200000 |
| 29 | 4 | 183950001-184250000 |
| 30 | 5 | 2400001-2800000 |
| 31 | 5 | 134800001-135050000 |
| 32 | 7 | 65150001-65350000 |
| 33 | 8 | 30200001-30600000 |
| 34 | 8 | 10200001-11250000 |
| 35 | 9 | 100200001-100550000 |
| 36 | 10 | 500001-800000 |
| 37 | 10 | 114450001-114750000 |
| 38 | 10 | 123650001-124100000 |
| 39 | 12 | 127350001-127950000 |
| 40 | 15 | 72150001-72400000 |
| 41 | 16 | 68250001-68800000 |
| 42 | 16 | 19350001-19800000 |
| 43 | 16 | 49650001-49950000 |
| 44 | 16 | 13050001-13500000 |
| 45 | 20 | 47500001-47900000 |
| 46 | 22 | 31000001-31200000 |
| 47 | 1 | 86600001-87150000 |
| 48 | 1 | 69650001-70250000 |
| 49 | 2 | 34550001-35100000 |
| 50 | 3 | 154600001-154950000 |
| 51 | 3 | 107600001-107850000 |
| 52 | 5 | 85650001-85950000 |
| 53 | 6 | 142250001-142450000 |

-continued

| | chromosome | region |
|---|---|---|
| 54 | 6 | 106850001-107000000 |
| 55 | 7 | 87000001-87350000 |
| 56 | 9 | 75350001-75600000 |
| 57 | 10 | 68500001-69050000 |
| 58 | 17 | 42750001-43100000 |
| 59 | 19 | 19850001-20300000 |
| 60 | 20 | 8000001-8250000 |
| 61 | 1 | 180850001-181100000 |
| 62 | 2 | 234900001-235400000 |
| 63 | 2 | 105100001-105400000 |
| 64 | 3 | 53950001-54200000 |
| 65 | 4 | 183900001-184300000 |
| 66 | 5 | 173400001-173700000 |
| 67 | 6 | 163600001-163850000 |
| 68 | 7 | 129100001-129550000 |
| 69 | 7 | 65150001-65350000 |
| 70 | 7 | 98000001-98650000 |
| 71 | 7 | 153600001-153950000 |
| 72 | 8 | 10200001-11400000 |
| 73 | 8 | 30200001-30700000 |
| 74 | 8 | 124600001-124950000 |
| 75 | 9 | 100150001-100650000 |
| 76 | 10 | 500001-800000 |
| 77 | 10 | 123650001-124200000 |
| 78 | 10 | 114450001-114750000 |
| 79 | 12 | 127350001-128100000 |
| 80 | 15 | 72150001-72400000, and |
| 81 | 16 | 78050001-78250000; |

(c) identifying the patient as having colon cancer when the level of the first and/or the second cell free DNA sequence is at least two standard deviations above the index value for a chromosomal region 1-60, or is at least two standard deviations below the index value for a chromosomal region 61-81; and (d) treating the patient with a therapy for colorectal cancer comprising at least one chemotherapeutic agent selected from the group consisting of fluorouracil, leucovorin, oxaliplatin, and capecitabine; and/or at least one monoclonal antibody selected from the group consisting of bevacizumab, cetuximab, and panitumumab.

2. The method of claim 1, further comprising determining in said sample the level of a third cell-free DNA having a sequence at least 25 nucleotides in length unambiguously assigned to a third chromosomal region selected from the group set forth in (b), wherein said third chromosomal region is different from said first and second chromosomal regions.

3. The method of claim 1, further comprising measuring in said sample the level of at least 5, 8, 10, 15, or 20 additional different cell free DNAs, each having a sequence at least 25 nucleotides in length and free of repetitive elements, wherein each sequence is unambiguously assigned to a different chromosomal region selected from the group set forth in (b).

4. The method of claim 1, wherein said patient has previously been treated with a therapy for colorectal cancer.

5. A method of treating a patient for colon cancer, the method comprising:
(a) identifying that a human patient that has or is suspected of having colon cancer has a change in copy number of at least two standard deviations from an index value from a normal subject of a cell-free DNA having a sequence of at least 25 nucleotides in length unambiguously assigned to a chromosomal region selected from the group consisting of chromosomal regions as follows, said regions numbered according to National Center for Biotechnology Information *Homo sapiens* hg18/Build 36.1:

| chromosome | region |
|---|---|
| 1 | 69800001-70200000 |
| 1 | 196550001-196800000 |
| 2 | 34550001-34950000 |
| 3 | 154600001-155050000 |
| 3 | 34350001-34550000 |
| 3 | 133900001-134350000 |
| 4 | 27550001-27800000 |
| 5 | 18650001-18950000 |
| 5 | 85650001-85950000 |
| 5 | 90850001-91100000 |
| 6 | 114250001-114550000 |
| 7 | 87000001-87300000 |
| 7 | 11350001-11700000 |
| 7 | 19600001-20100000 |
| 7 | 95100001-95400000 |
| 8 | 51450001-52000000 |
| 8 | 61100001-61450000 |
| 8 | 82850001-83200000 |
| 9 | 75350001-75600000 |
| 12 | 44700001-45050000 |
| 14 | 21350001-22050000 |
| 1 | 180850001-181150000 |
| 2 | 234900001-235400000 |
| 2 | 26950001-27450000 |
| 2 | 95200001-95550000 |
| 2 | 105100001-105400000 |
| 3 | 53950001-54200000 |
| 3 | 140050001-140200000 |
| 4 | 183950001-184250000 |
| 5 | 2400001-2800000 |
| 5 | 134800001-135050000 |
| 7 | 65150001-65350000 |
| 8 | 30200001-30600000 |
| 8 | 10200001-11250000 |
| 9 | 100200001-100550000 |
| 10 | 500001-800000 |
| 10 | 114450001-114750000 |
| 10 | 123650001-124100000 |
| 12 | 127350001-127950000 |
| 15 | 72150001-72400000 |
| 16 | 68250001-68800000 |
| 16 | 19350001-19800000 |
| 16 | 49650001-49950000 |
| 16 | 13050001-13500000 |
| 20 | 47500001-47900000 |
| 22 | 31000001-31200000 |
| 1 | 86600001-87150000 |
| 1 | 69650001-70250000 |
| 2 | 34550001-35100000 |
| 3 | 154600001-154950000 |
| 3 | 107600001-107850000 |
| 5 | 85650001-85950000 |
| 6 | 142250001-142450000 |
| 6 | 106850001-107000000 |
| 7 | 87000001-87350000 |
| 9 | 75350001-75600000 |
| 10 | 68500001-69050000 |
| 17 | 42750001-43100000 |
| 19 | 19850001-20300000 |
| 20 | 8000001-8250000 |
| 1 | 180850001-181100000 |
| 2 | 234900001-235400000 |
| 2 | 105100001-105400000 |
| 3 | 53950001-54200000 |
| 4 | 183900001-184300000 |
| 5 | 173400001-173700000 |
| 6 | 163600001-163850000 |
| 7 | 129100001-129550000 |
| 7 | 65150001-65350000 |
| 7 | 98000001-98650000 |
| 7 | 153600001-153950000 |
| 8 | 10200001-11400000 |
| 8 | 30200001-30700000 |
| 8 | 124600001-124950000 |

-continued

| chromosome | region |
|---|---|
| 9 | 100150001-100650000 |
| 10 | 500001-800000 |
| 10 | 123650001-124200000 |
| 10 | 114450001-114750000 |
| 12 | 127350001-128100000 |
| 15 | 72150001-72400000, and |
| 16 | 78050001-78250000; | by:
 (i) obtaining or having obtained a nucleic acid sample from blood, serum, or plasma from the patient and
 (ii) performing or having performed sequencing of nucleic acids obtained from the nucleic acid sample to determine copy number changes of the cell free DNA by determining the level of a nucleic acid sequence of at least 25 nucleotides in length that is unambiguously assigned to each of chromosomal regions set forth in the group of chromosomal regions;
(b) identifying that the patient has:
(i) an increase in copy number of a sequence of at least 25 nucleotides in length unambiguously assigned to:

| Chromosome | Region |
|---|---|
| 1 | 69800001-70200000 |
| 1 | 196550001-196800000 |
| 2 | 34550001-34950000 |
| 3 | 154600001-155050000 |
| 3 | 34350001-34550000 |
| 3 | 133900001-134350000 |
| 4 | 27550001-27800000 |
| 5 | 18650001-18950000 |
| 5 | 85650001-85950000 |
| 5 | 90850001-91100000 |
| 6 | 114250001-114550000 |
| 7 | 87000001-87300000 |
| 7 | 11350001-11700000 |
| 7 | 19600001-20100000 |
| 7 | 95100001-95400000 |
| 8 | 51450001-52000000 |
| 8 | 61100001-61450000 |
| 8 | 82850001-83200000 |
| 9 | 75350001-75600000 |
| 12 | 44700001-45050000 |
| 14 | 21350001-22050000 |
| 1 | 86600001-87150000 |
| 1 | 69650001-70250000 |
| 2 | 34550001-35100000 |
| 3 | 154600001-154950000 |
| 3 | 107600001-107850000 |
| 5 | 85650001-85950000 |
| 6 | 142225001-142450000 |
| 6 | 106850001-107000000 |
| 7 | 87000001-87350000 |
| 9 | 75350001-75600000 |
| 10 | 68500001-69050000 |
| 17 | 42750001-43100000 |
| 19 | 19850001-20300000, or |
| 20 | 8000001-8250000; or |

(ii) has a decrease in copy number of a sequence of at least 25 nucleotides in length unambiguously assigned to

| chromosome | region |
|---|---|
| 1 | 180850001-181150000 |
| 2 | 234900001-235400000 |
| 2 | 26950001-27450000 |
| 2 | 95200001-95550000 |
| 2 | 105100001-105400000 |
| 3 | 53950001-54200000 |
| 3 | 140050001-140200000 |
| 4 | 183950001-184250000 |
| 5 | 2400001-2800000 |
| 5 | 134800001-135050000 |
| 7 | 65150001-65350000 |
| 8 | 30200001-30600000 |
| 8 | 10200001-11250000 |
| 9 | 100200001-100550000 |
| 10 | 500001-800000 |
| 10 | 114450001-114750000 |
| 10 | 123650001-124100000 |
| 12 | 127350001-127950000 |
| 15 | 72150001-72400000 |
| 16 | 68250001-68800000 |
| 16 | 19350001-19800000 |
| 16 | 49650001-49950000 |
| 16 | 13050001-13500000 |
| 20 | 47500001-47900000 |
| 22 | 31000001-31200000 |
| 1 | 180850001-181100000 |
| 2 | 234900001-235400000 |
| 2 | 105100001-105400000 |
| 3 | 53950001-54200000 |
| 4 | 183900001-184300000 |
| 5 | 173400001-173700000 |
| 6 | 163600001-163850000 |
| 7 | 129100001-129550000 |
| 7 | 65150001-65350000 |
| 7 | 98000001-98650000 |
| 7 | 153600001-153950000 |
| 8 | 10200001-11400000 |
| 8 | 30200001-30700000 |
| 8 | 124600001-124950000 |
| 9 | 100150001-100650000 |
| 10 | 500001-800000 |
| 10 | 123650001-124200000 |
| 10 | 114450001-114750000 |
| 12 | 127350001-128100000 |
| 15 | 72150001-72400000 or |
| 16 | 78050001-78250000 | and
(c) administering a therapy for colon cancer comprising at least one chemotherapeutic agent selected from the group consisting of fluorouracil, leucovorin, oxaliplatin, and capecitabine; and/or at least one monoclonal antibody selected from the group consisting of bevacizumab, cetuximab, and panitumumab.

* * * * *